United States Patent [19]

Kunitz et al.

[11] Patent Number: 5,009,985
[45] Date of Patent: Apr. 23, 1991

[54] IRON COMPLEXES AND BLEACHING BATHS CONTAINING SAME

[75] Inventors: Friedrich-Wilhelm Kunitz, Leverkusen; Ralf Wichmann, Cologne, both of Fed. Rep. of Germany

[73] Assignee: Agfa-Gevaert Aktiengesellschaft, Leverkusen, Fed. Rep. of Germany

[21] Appl. No.: 571,504

[22] Filed: Aug. 22, 1990

[51] Int. Cl.$^5$ ................................................ G03C 5/44
[52] U.S. Cl. ........................................ 430/430; 430/460; 430/461; 556/139; 556/147; 556/148
[58] Field of Search ............. 430/430, 431, 460, 461, 430/462, 393, 400, 479, 491; 556/139, 147, 148; 562/414, 430, 452, 453, 455

[56] References Cited

U.S. PATENT DOCUMENTS

| | | | |
|---|---|---|---|
| 2,892,867 | 6/1959 | Williams et al. | 562/452 |
| 3,742,002 | 6/1973 | Ohlson et al. | 556/139 |
| 3,867,419 | 2/1975 | Iwano et al. | 556/148 |
| 4,746,507 | 5/1988 | Quag | 556/148 |

OTHER PUBLICATIONS

Chemical Abstract 68/83909f, 1968.
Chemical Abstract 108/218457z, 1988.
Chemical Abstract 110/210196j, 1989.

*Primary Examiner*—Hoa Van Le
*Attorney, Agent, or Firm*—Connollly & Hutz

[57] ABSTRACT

Iron(III)-complexes of compounds of the formula

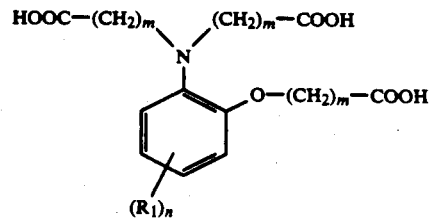

wherein
$R_1$ denotes a substituent,
m denotes 1 or 2 and
n denotes 0, 1 or 2 are valuable and biodegradable bleaching agents for photographic elements.

7 Claims, No Drawings

IRON COMPLEXES AND BLEACHING BATHS CONTAINING SAME

This invention relates to novel iron complexes which are excellently suitable for bleaching baths for the processing of photographic elements, particularly color photographic elements.

It is customary to use iron (III) complexes of ethylene diaminotetraacetic acid (EDTA), 1,3-propylene diaminotetraacetic acid (PDTA), diethylene triaminopentaacetic acid (DTPA) and others, mostly as ammonium salts, as the active ingredients in bleaching baths for the processing of silver halide color elements.

The iron (III) ammonium complex salts of EDTA and of mixtures of EDTA and PDTA are used, in practice due to the reduction of the blaching time obtained therewith.

EDTA and PDTA do, however, have the disadvantage of not being readily biodegradable.

The object of the invention is to find bleaching substances which on the one hand are comparable with the compounds used in practice with respect to their bleaching action (bleaching force and bleaching time) and which are on the other hand readily biodegradable.

It was surprisingly found that these conditions are fulfilled by the hitherto unknown iron (III) complex of the polycarboxylic acids of formula (I)

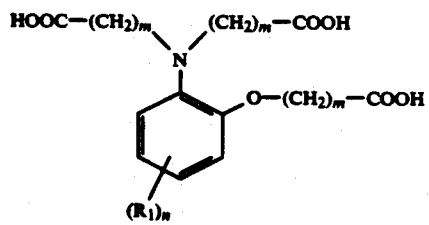

wherein
R₁ denotes a substituent,
m denotes 1 or 2 and
n denotes 0, 1 or 2.

The present invention therefore relates to iron (III) complexes of compounds of formula (I).

Suitable substituents $R_1$ are for example halogen such as chlorine and bromine, alkyl, preferably with 1 to 4 carbon atoms, aminosulfonyl which is mono- or di-substituted on the nitrogen atom, for example by $C_1$ to $C_4$-alkyl or benzyl, aminocarbonyl, optionally substituted by $C_1$ to $C_4$-alkyl or benzyl, carboxy, sulfo or cyano.

Preferably n is 0 or 1 and most preferably is 0; preferably m is 1.

The compounds of formula 1 and their preparation are known from U.S. Pat. No. 2,892,867.

Particularly suitable compounds are:

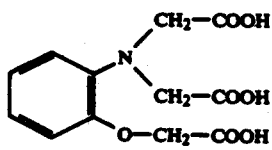

1.

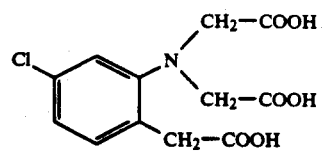

2.

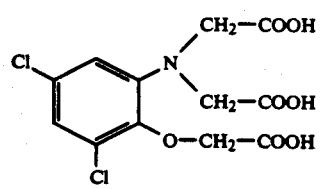

3.

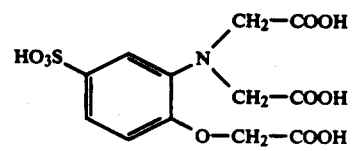

4.

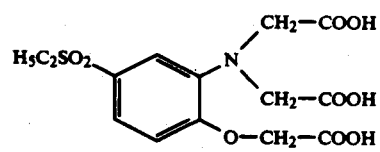

5.

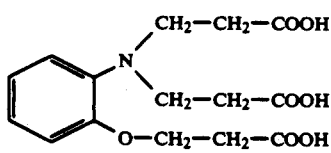

6.

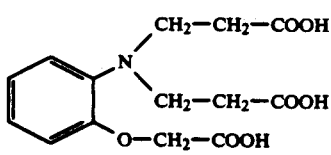

7.

The invention further relates to bleaching baths containing an iron complex of a compound of formula I in an active amount for the processing of photographic silver halide elements, especially of color photographic silver halide elements. The term "bleaching baths" includes bleach fixing baths, wherein the process steps bleaching (oxidation of silver to silver salts) and fixing (dissolution of the silver salts) are combined.

The bleaching baths according to the invention contain the iron complexes usually in an amount of from 0.01 to 1 mol/l. Additionally the bleaching baths can contain further iron complexes or iron complex salts having bleaching power, preferably of polycarboxylic acids which are readily biodegradable.

In a preferred embodiment of the invention the iron complex of nitrilo triacetic acid is used as a further bleaching agent, preferably in an amount of from 0.01 to 1 mol/l. The mixture of bleaching agents contains at least 30 mol-%, preferably at least 50 mol-% of the iron complex of compounds of formula (I).

The mixture of the iron complexes according to the invention with the iron complex of nitrilo triacetic acid is characterized by excellent stability and a bleaching time which is surprisingly shorter than the average expected from the bleaching times of the single components.

The bleaching baths according to the invention can be used for the bleaching elements, in which metallic silver has been produced by development. Preferably they are used for the bleaching of color photographic silver halide materials such as color negative film, color reversal film, color negative paper, color reversal paper and direct positive color elements, independent of their structure, their silver halide composition and the structure of dye producing couplers and the dyes produced thereof.

Particularly the cyan dyes, which are easily transformed into the colorless leuco dyes by improper treatment, are not affected by the inventive bleaching baths.

EXAMPLES

In the following examples a color negative film having a support of cellulose triacetate and at least a blue-, green- and red-sensitive layer was used. The silver bromide iodide emulsions had an iodide content of 6 mol-%. The film was exposed, developed and bleached with different bleaching baths having the same molar concentration of oxidizing agent. The bleaching time necessary to reach a residual silver content of less than 0.1% was determined. The results are shown in Table 1.

| Example 1 | |
|---|---|
| Ammonium-iron complex salt of EDTA | 98 g |
| EDTA | 4 g |
| Ammoniumbromide | 150 g |
| Ammoniumnitrate | 16 g |
| Make up with water to 1 liter | |
| pH | 6.0 |

| Example 2 | |
|---|---|
| Ammonium iron complex salt of EDTA | 65 g |
| Ammonium iron complex salt of PDTA | 34 g |
| EDTA | 4 g |
| NH$_4$Br | 150 g |
| NH$_4$NO$_3$ | 16 g |
| Make up with water to 1 liter | |
| pH | 5.15 |

| Example 3 | |
|---|---|
| Iron complex of nitrilo triacetic acid | 66 g |
| Nitrilo triacetic acid | 4 g |
| NH$_4$Br | 150 g |
| NH$_4$NO$_3$ | 16 g |
| Make up with water to 1 liter | |
| pH | 4.0 |

| Example 4 | |
|---|---|
| Iron complex of complexing agent 1 | 89 g |
| Complexing agent 1 | 4 g |
| NH$_4$Br | 150 g |

| Example 4 -continued | |
|---|---|
| NH$_4$NO$_3$ | 16 g |
| Make up with water to 1 liter | |
| pH | 4.0 |

| Example 5 | |
|---|---|
| Iron complex of complexing agent 1 | 44.5 g |
| Iron complex of nitrilo triacetic acid | 33 g |
| Nitrilo triacetic acid | 4 g |
| NH$_4$Br | 150 g |
| NH$_4$NO$_3$ | 16 g |
| Make up with water to 1 liter | |
| pH | 4.0 |

TABLE 1

| Example | Bleaching time |
|---|---|
| 1(Comparison) | 3.0 min |
| 2(Comparison) | 2.0 min |
| 3(Comparison) | 4.5 min |
| 4(Invention) | 1.0 min |
| 5(Invention) | 1.5 min |

We claim:

1. Iron(III)-complexes of compounds of the formula

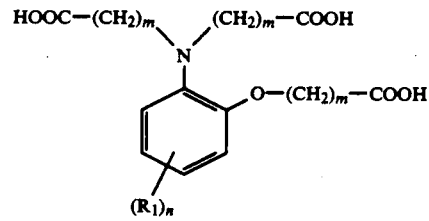

wherein
R$_1$ denotes a substituent,
m denotes 1 or 2 and
n denotes 0, 1 or 2.

2. Iron(III) complexes according to claim 1, wherein R$_1$ denotes halogen, C$_1$ to C$_4$alkyl, aminosulfonyl, aminocarbonyl, carboxy, sulfo or cyano,
m denotes 1 and
n denotes 0 or 1.

3. Bleaching bath for the processing of photographic elements containing an active quantity of an iron(III)-complex according to claim 1.

4. Bleaching bath according to claim 3 containing an active quantity of an iron(III) complex according to claim 2.

5. Bleaching bath according to claim 3 containing the iron(III)-complex in an amount of from 0.01 to 1 mol/l.

6. Bleaching bath according to claim 3 additionally containing the iron(III) complex of nitrilo triacetic acid, the mixture of bleaching agents containing the iron(III) complex of claim 1 at least in an amount of 30 mol-%.

7. Bleaching agent of claim 5 containing the iron(III)-complex of nitrilo triacetic acid in an amount of from 0.01 to 1 mol/l.

* * * * *